(12) United States Patent
Fukushi et al.

(10) Patent No.: US 11,079,402 B2
(45) Date of Patent: Aug. 3, 2021

(54) AUTOMATIC ANALYZING APPARATUS, AND METHOD FOR DETECTING FLOW PATH CLOGGING OF THE AUTOMATIC ANALYZING APPARATUS

(71) Applicant: HITACHI HIGH-TECH CORPORATION, Tokyo (JP)

(72) Inventors: Yudai Fukushi, Tokyo (JP); Takamichi Mori, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 0 days.

(21) Appl. No.: 16/645,600

(22) PCT Filed: Jan. 23, 2019

(86) PCT No.: PCT/JP2019/001964
§ 371 (c)(1),
(2) Date: Mar. 9, 2020

(87) PCT Pub. No.: WO2019/176295
PCT Pub. Date: Sep. 19, 2019

(65) Prior Publication Data
US 2020/0278373 A1      Sep. 3, 2020

(30) Foreign Application Priority Data
Mar. 15, 2018  (JP) .............................. JP2018-047432

(51) Int. Cl.
*G01N 35/10*     (2006.01)
*A61B 1/00*      (2006.01)
(Continued)

(52) U.S. Cl.
CPC ..... *G01N 35/1095* (2013.01); *G01N 35/1016* (2013.01); *A61B 1/00* (2013.01);
(Continued)

(58) Field of Classification Search
CPC ........... G01N 35/1095; G01N 35/1016; G01N 35/00; G01N 35/00623;
(Continued)

(56) References Cited

U.S. PATENT DOCUMENTS

| | | | |
|---|---|---|---|
| 4,730,999 A * | 3/1988 | Tsukuda | F04B 41/02 417/44.3 |
| 2009/0041628 A1 * | 2/2009 | Kakizaki | G01N 35/1004 422/68.1 |

(Continued)

FOREIGN PATENT DOCUMENTS

| | | |
|---|---|---|
| JP | H6209901 A | 8/1994 |
| JP | H0938029 A | 2/1997 |

(Continued)

OTHER PUBLICATIONS

Search Report dated Apr. 9, 2019 in corresponding International Application No. PCT/JP2019/001964.

(Continued)

*Primary Examiner* — Kathryn Wright
*Assistant Examiner* — Curtis A Thompson
(74) *Attorney, Agent, or Firm* — Miles & Stockbridge, P.C.

(57) ABSTRACT

Provided is an automatic analyzer that has a plurality of mechanisms including a mechanism that suctions reaction waste liquid and a mechanism that suctions cleaning liquid, etc. on a sample and a probe surface, the automatic analyzer reducing pressure in a vacuum tank using a pressure-reducing pump, etc., and suctioning waste liquid by negative pressure in the vacuum tank. A contact point of a vacuum switch that is provided in the vacuum tank is closed when the pressure in the vacuum tank reaches a specified negative pressure, and then the analyzer becomes ready for analysis. If any flow path portion of any mechanism that connects (Continued)

with the vacuum tank becomes clogged, suctioning operation cannot be performed properly and analysis performance is affected. The vacuum pump is switched off at a timing at which each solenoid valve connecting to the vacuum pump is individually opened, and the time that elapses before the pressure in the vacuum tank reaches the specified negative pressure is measured. The measured time is compared with parameters in a normal case, and the presence or absence of an anomaly is determined.

7 Claims, 8 Drawing Sheets

(51) Int. Cl.
G01N 33/543 (2006.01)
G01N 35/02 (2006.01)
G01N 35/00 (2006.01)
B23Q 17/09 (2006.01)
G01F 1/74 (2006.01)
G08B 21/18 (2006.01)
B23Q 11/10 (2006.01)
G01M 1/36 (2006.01)

(52) U.S. Cl.
CPC .............. *B23Q 11/10* (2013.01); *B23Q 17/09* (2013.01); *G01F 1/74* (2013.01); *G01M 1/36* (2013.01); *G01N 33/543* (2013.01); *G01N 35/00* (2013.01); *G01N 35/00623* (2013.01); *G01N 35/00871* (2013.01); *G01N 35/02* (2013.01); *G01N 35/10* (2013.01); *G01N 35/1002* (2013.01); *G01N 2035/00633* (2013.01); *G08B 21/18* (2013.01)

(58) Field of Classification Search
CPC ..... G01N 2035/00633; G01N 35/1002; G01N 35/00871; G01N 33/543; G01N 35/02; G01N 35/10; B23Q 17/09; B23Q 11/10; G01F 1/74; G08B 21/18; G01M 1/36
See application file for complete search history.

(56) References Cited

U.S. PATENT DOCUMENTS

| 2015/0224503 | A1* | 8/2015 | Dulaff | H05B 6/108 219/630 |
| 2015/0362514 | A1* | 12/2015 | Tamezane | G01N 35/00623 422/509 |
| 2018/0015583 | A1 | 1/2018 | Faverjon et al. | |
| 2019/0339296 | A1* | 11/2019 | Mori | G01N 35/1004 |

FOREIGN PATENT DOCUMENTS

| JP | 200046846 A | | 2/2000 |
| JP | 2015081909 A | * | 4/2015 |
| JP | 2016003967 A | * | 1/2016 |
| JP | 2018503835 A | | 2/2018 |
| WO | 2007132632 A1 | | 11/2007 |
| WO | 2014119525 A1 | | 8/2014 |

OTHER PUBLICATIONS

Written Opinion dated Apr. 9, 2020 in corresponding International Application No. PCT/JP2019/001964.
International Search Report dated Apr. 9, 2019 with English Translation, issued in counterpart International Application No. PCT/JP2019/001964.

* cited by examiner

[FIG. 1]
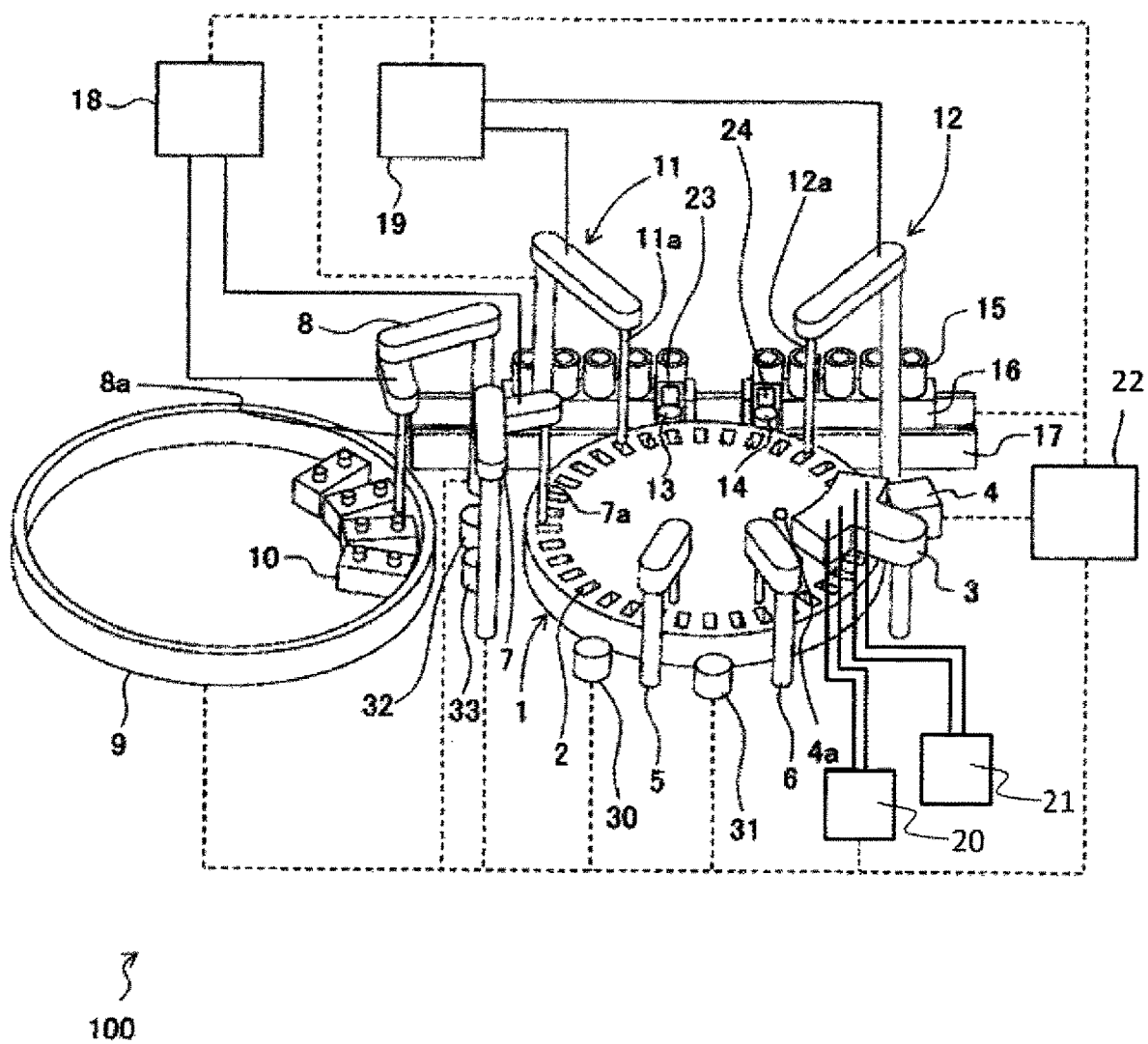

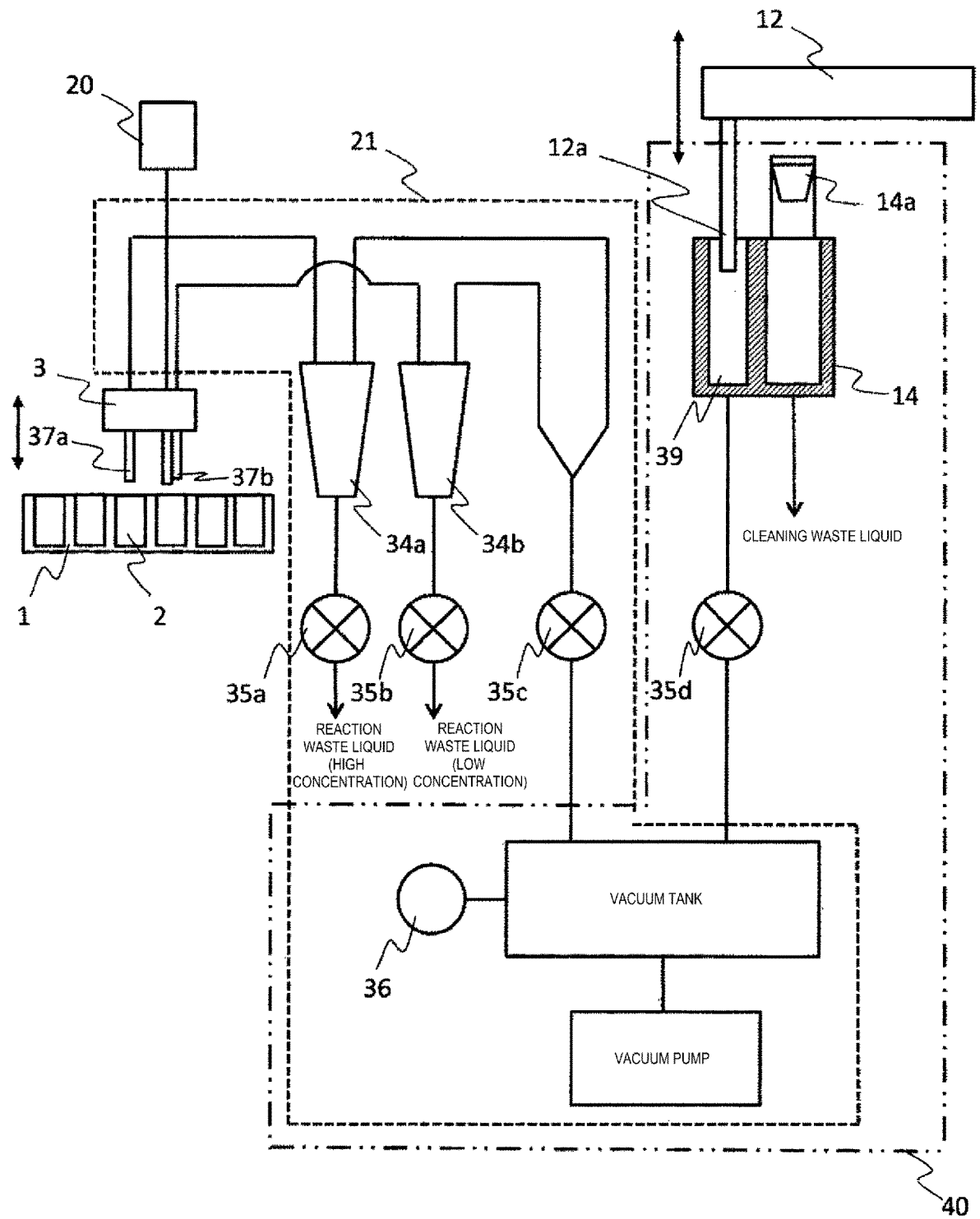
[FIG. 2]

[FIG. 3A]
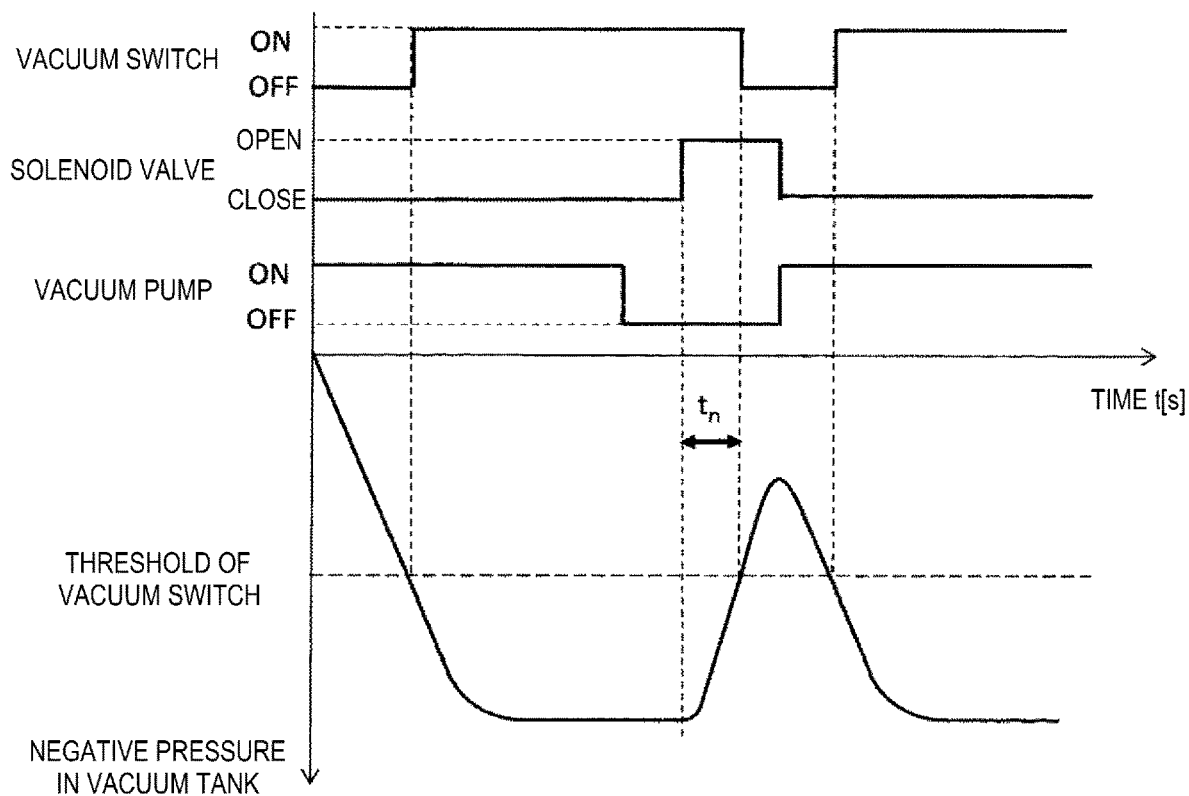

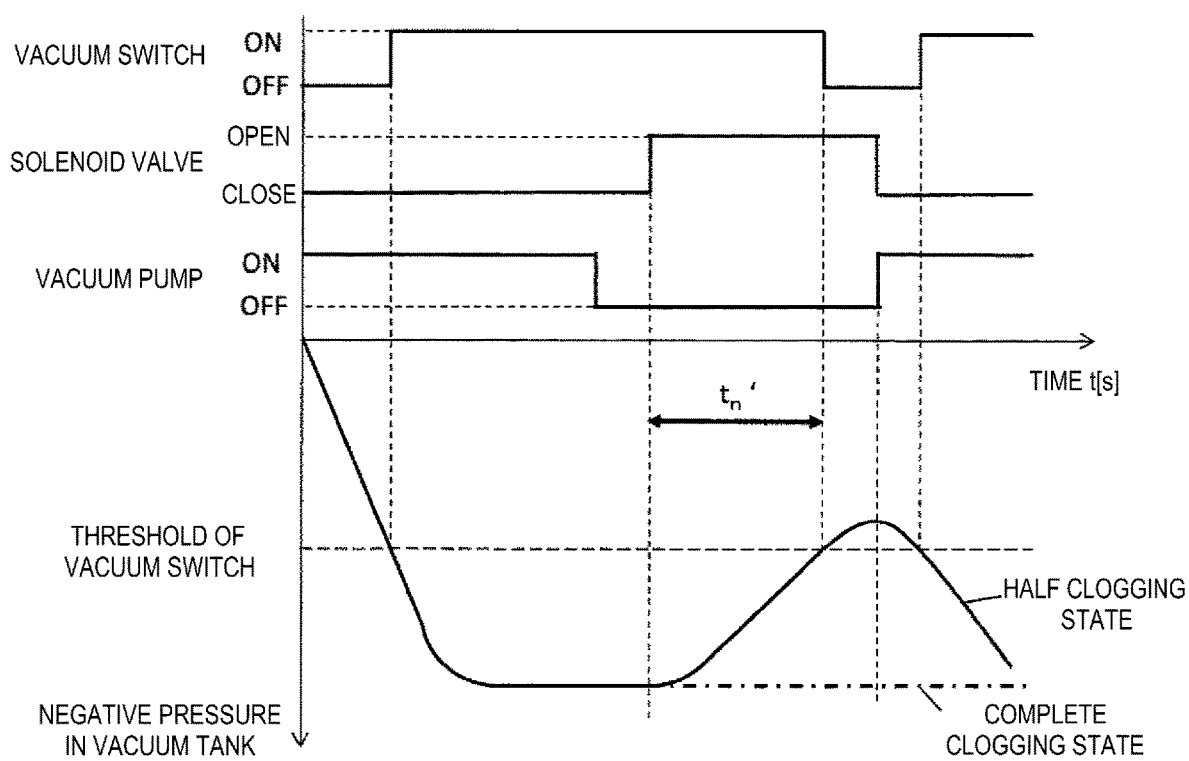
[FIG. 3B]

[FIG. 4A]
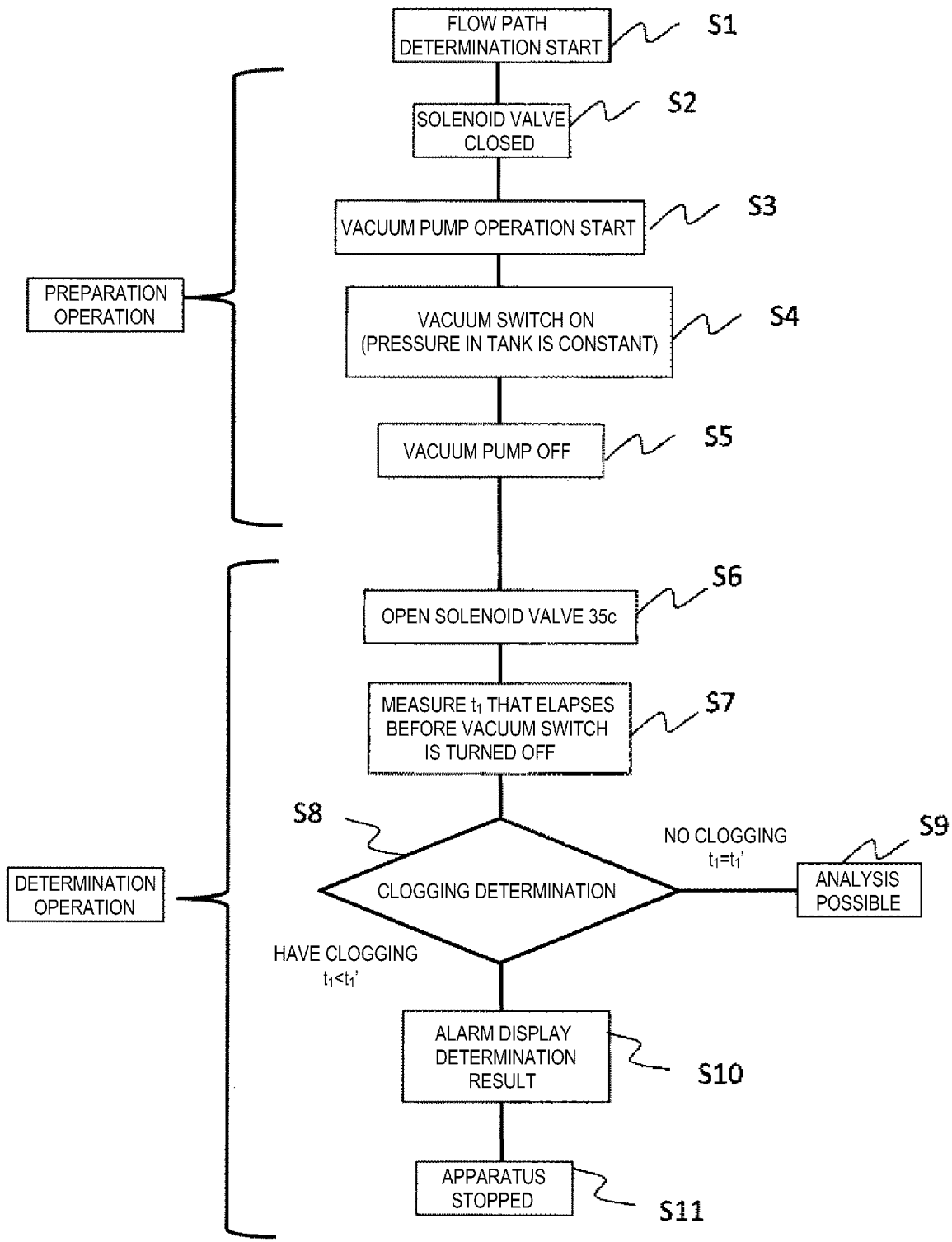

[FIG. 4B]
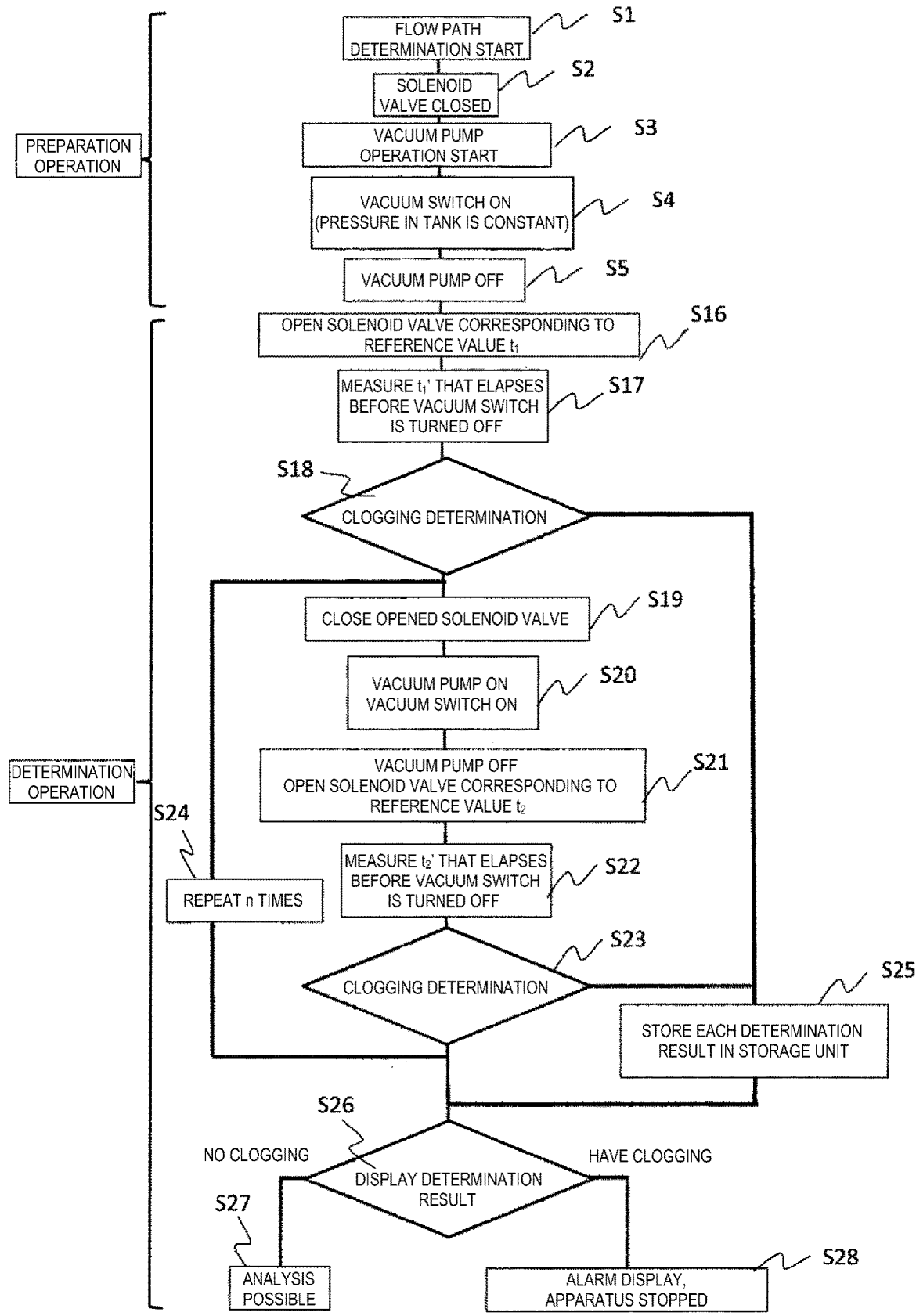

[FIG. 5]
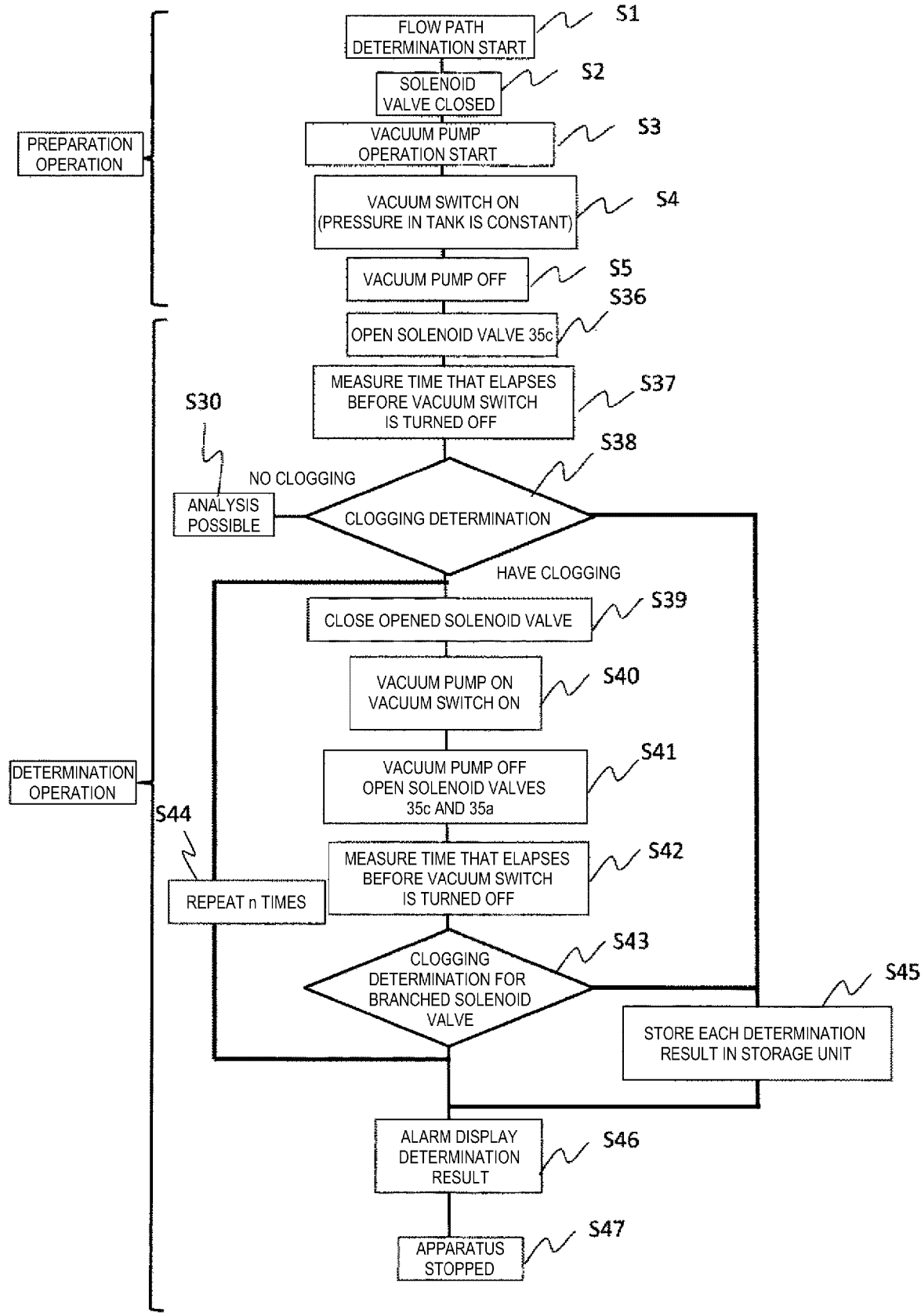

[FIG. 6]
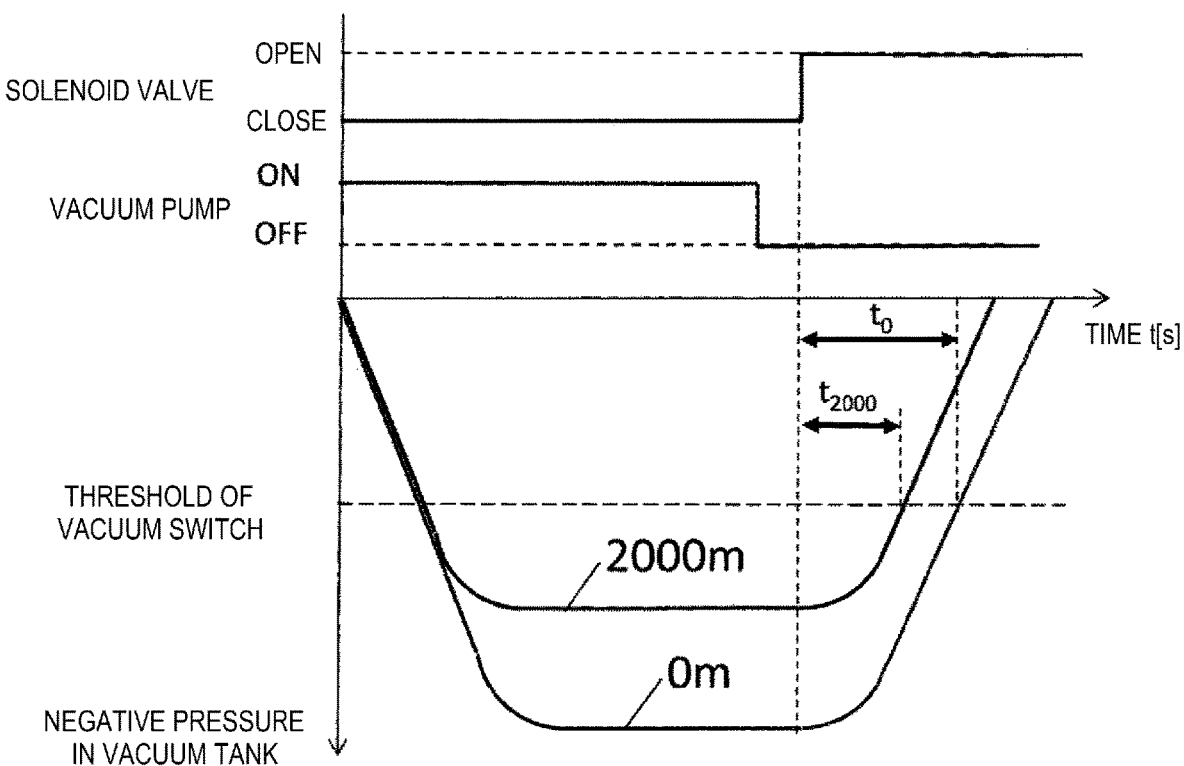

AUTOMATIC ANALYZING APPARATUS, AND METHOD FOR DETECTING FLOW PATH CLOGGING OF THE AUTOMATIC ANALYZING APPARATUS

TECHNICAL FIELD

The present invention relates to an automatic analyzer, and a method for detecting flow path clogging of the automatic analyzer.

BACKGROUND ART

An automatic analyzer discharges a certain amount of sample and a certain amount of reagent into a reaction vessel, mixes the sample and the reagent to cause reaction, and analyzes a component, a concentration, and the like of the sample by optically measuring reaction liquid.

After completion of the analysis, since reaction waste liquid in which the sample and the reagent are reacted is generated in the reaction vessel, the waste liquid is suctioned using a vacuum pump or the like in order to remove the reaction waste liquid from the reaction vessel. In addition, in the automatic analyzer that performs qualitative and quantitative analysis of the sample, by appropriately cleaning a probe used for dispensing the sample to be analyzed, occurrence of cross contamination is prevented and analysis accuracy is maintained, and a cleaning liquid suction mechanism that removes cleaning liquid or the like adhered to a probe surface is also provided.

CITATION LIST

Patent Literature

Patent Literature 1: WO 07/132632

SUMMARY OF INVENTION

Technical Problem

The automatic analyzer having a plurality of mechanisms including a mechanism for suctioning the reaction waste liquid and a mechanism for suctioning the cleaning liquid and the like adhered to the surface after probe cleaning, reduces pressure in a vacuum tank by a pressure-reducing pump or the like, arranges a solenoid valve in a flow path from the vacuum tank, opens and closes the solenoid valve, and suctions the waste liquid by a pressure difference in the vacuum tank. When the pressure in the vacuum tank reaches specified negative pressure, a contact point of a vacuum switch provided in the vacuum tank is switched and then the analyzer becomes ready for analysis. When a flow path portion of each mechanism connected to the vacuum tank is clogged or an operation failure occurs in the solenoid valve, the suction operation cannot be performed normally, and there is a high possibility that the analysis performance will be affected due to such as waste liquid remaining in the reaction vessel or remaining cleaning water adhered to a probe. In the automatic analyzer disclosed in Patent Literature 1, an individual pressure sensor is installed in a suction nozzle in order to detect clogging of a drainage system of a waste liquid suction unit. In this case, the pressure sensor is required for all of the waste liquid suction units, and the risk of failure increases as the number of sensors increases. Further, in an existing apparatus that does not have a pressure sensor, when a clogging detection function is to be newly added, an installation location of the pressure sensor is limited, and an apparatus configuration is complicated.

An object of the invention is to provide an automatic analyzer capable of detecting clogging in a flow path and a method for detecting flow path clogging of the automatic analyzer.

Solution to Problem

To solve the above problems, an automatic analyzer of the invention includes a vacuum tank and a vacuum pump that vacuum suctions liquid; a first solenoid valve provided in a flow path connected to the vacuum tank; a determination unit that determines whether a vacuum value in the vacuum tank is equal to or greater than a predetermined threshold, or whether the vacuum value is smaller than the predetermined threshold; and a clogging detection unit that detects clogging in the flow path. The clogging detection unit changes the vacuum pump from ON to OFF with the first solenoid valve being in a closed state, and thereafter, changes the first solenoid valve from the closed state to an open state, and detects presence and absence of clogging in the flow path by comparing time that elapses before the determination unit determines that the vacuum value in the vacuum tank is equal to or greater than the predetermined threshold from a time point when the first solenoid valve is changed from the closed state to the open state, to a predetermined threshold.

In order to solve the above problems, with a solenoid valve arranged between a vacuum tank and a mechanism requiring vacuum being in a closed state, a vacuum pump is operated until negative pressure of the vacuum tank becomes constant, and then the vacuum pump is stopped. A negative pressure value in the vacuum tank is held at a constant negative pressure value unless there is a normal leak. If the vacuum switch is turned OFF at a certain time, a leak occurs somewhere in the flow path. Therefore, in order to confirm whether there is a leak in each flow path system, the vacuum pump is stopped when the negative pressure of the vacuum tank is constant, the solenoid valve in the flow path at apart desired to be confirmed and connected to the vacuum tank is opened, and time that elapses before the vacuum switch is turned OFF is measured, and presence and absence of an anomaly in the flow path system is determined by comparing the measured time with a threshold. By performing the above-described determination in all the flow paths using vacuum, presence and absence of an anomaly in the flow path system is determined.

Advantageous Effect

According to the invention, when there is an anomaly in the flow path, the anomaly of the flow path can be detected without using a sensor for measuring the pressure.

BRIEF DESCRIPTION OF DRAWINGS

FIG. 1 is a diagram showing an outline of an automatic analyzer according to an embodiment of the invention.

FIG. 2 is a schematic diagram illustrating a connection between a waste liquid suction mechanism and a vacuum tank according to the embodiment of the invention.

FIG. 3A is a diagram showing waveforms of, when the suction mechanism is normal without clogging, pressure, opening and closing of a solenoid valve, ON/OFF of a vacuum pump and a signal of a vacuum switch at a time of suctioning the waste liquid.

FIG. 3B is a diagram showing waveforms of, when the suction mechanism is clogged, the pressure, the opening and closing of the solenoid valve, the ON/OFF of the vacuum pump, and the signal of the vacuum switch at the time of suctioning the waste liquid.

FIG. 4A is a diagram showing a flowchart of determining clogging in a mechanism that suctions cleaning waste liquid.

FIG. 4B is a diagram showing a flowchart of determining clogging when the mechanism that suctions the cleaning waste liquid is connected to n or more (n=2) vacuum tanks.

FIG. 5 shows a flowchart of determining clogging when a flow path between a solenoid valve and a nozzle connected to the vacuum tank in a mechanism that suctions reaction waste liquid is branched.

FIG. 6 shows a relationship between pressure in the vacuum tank and an altitude when a clogging determination method is used.

DESCRIPTION OF EMBODIMENTS

In an automatic analyzer of the invention, with a solenoid valve arranged between a vacuum tank and a mechanism requiring vacuum being in a closed state, a vacuum pump is operated until negative pressure of the vacuum tank becomes constant, and then the vacuum pump is stopped. A negative pressure value in the vacuum tank is held at a constant negative pressure value unless there is a normal leak. If a vacuum switch is turned OFF at a certain time, a leak occurs somewhere in the flow path. Therefore, in order to confirm whether there is a leak in each flow path system, the vacuum pump is stopped when the negative pressure of the vacuum tank is constant, the solenoid valve in the flow path at apart desired to be confirmed and connected to the vacuum tank is opened, and time that elapses before the vacuum switch is turned OFF is measured, and presence and absence of an anomaly in the flow path system is determined by comparing the measured time with a threshold. By performing the above-described determination in all the flow paths using vacuum, presence and absence of an anomaly in the flow path system is determined.

Hereinafter, an embodiment of an automatic analyzer and a method for cleaning a dispensing probe of the invention will be described in detail with reference to FIGS. 1 to 6.

First, an overall configuration of an automatic analyzer will be described with reference to FIG. 1. FIG. 1 is a diagram schematically showing the overall configuration of the automatic analyzer according to the present embodiment.

In FIG. 1, an automatic analyzer 100 is an apparatus that dispenses a sample and a reagent into a reaction vessel 2 separately to cause reaction, and measures the reacted liquid, and a schematic configuration of the automatic analyzer 100 includes a sample transport mechanism 17, a reagent disk 9, a reaction disk 1, a first sample dispensing mechanism 11, a second sample dispensing mechanism 12, reagent dispensing mechanisms 7, 8, stirring mechanisms 5, 6, a light source 4a, a spectrophotometer 4, a cleaning mechanism 3, and a control unit 22.

In the reaction disk 1, the reaction vessels 2 are arranged in a circumferential direction. The reaction vessel 2 is a vessel for accommodating mixed liquid in which the sample and the reagent are mixed, and a plurality of reaction vessels 2 are arranged on the reaction disk 1. In a vicinity of the reaction disk 1, the sample transport mechanism 17 that transports a sample rack 16 on which one or more sample vessels accommodating a sample to be analyzed are mounted is arranged.

The first sample dispensing mechanism 11 and the second sample dispensing mechanism 12 capable of rotating and moving up and down are arranged between the reaction disk 1 and the sample transport mechanism 17.

The first sample dispensing mechanism 11 has a sample probe 11a arranged with a tip thereof being directed downward, and a sample pump 19 is connected to the sample probe 11a. The first sample dispensing mechanism 11 is configured to be capable of discharging cleaning water (hereinafter referred to as "internal cleaning water"), sent from a cleaning water tank (not shown) by the sample pump 19, from the sample probe 11a. The first sample dispensing mechanism 11 is configured to be capable of horizontally rotating and moving up and down, inserts the sample probe 11a into the sample vessel 15 to suction the sample by operating the sample pump 19, and inserts the sample probe 11a into the reaction vessel 2 to discharge the sample. Thus, the sample is dispensed from the sample vessel 15 to the reaction vessel 2. In an operating range of the first sample dispensing mechanism 11, a cleaning tank 13 for cleaning the sample probe 11a with cleaning liquid and a cleaning vessel 23 for cleaning the sample probe 11a with special cleaning liquid are arranged. When a position where the sample probe 11a is inserted into the sample vessel 15 and the sample is suctioned is set as a first sample suction position, and a position where the sample probe 11a is inserted into the reaction vessel 2 and the sample is discharged is set as a first sample discharge position, the cleaning tank 13 and the cleaning vessel 23 are arranged between the first sample suction position and the first sample discharge position.

The second sample dispensing mechanism 12 has a sample probe 12a arranged with a tip thereof being directed downward, and the sample pump 19 is connected to the sample probe 12a. The second sample dispensing mechanism 12 is configured to be capable of discharging cleaning water (internal cleaning water), sent from the cleaning water tank (not shown) by the sample pump 19, from the sample probe 12a. The second sample dispensing mechanism 12 is configured to be capable of horizontally rotating and moving up and down, inserts the sample probe 12a into the sample vessel 15 to suction the sample by operating the sample pump 19, and inserts the sample probe 12a into the reaction vessel 2 to discharges the sample. Thus, the sample is dispensed from the sample vessel 15 to the reaction vessel 2. In an operating range of the second sample dispensing mechanism 12, a cleaning tank 14 for cleaning the sample probe 12a with cleaning liquid and a cleaning vessel 24 for cleaning the sample probe 12a with special cleaning liquid are arranged. When a position where the sample probe 12a is inserted into the sample vessel 15 and the sample is suctioned is set as a second sample suction position, and a position where the sample probe 12a is inserted into the reaction vessel 2 and the sample is discharged is set as a second sample discharge position, the cleaning tank 14 and the cleaning vessel 24 are arranged between the second sample suction position and the second sample discharge position.

The cleaning tanks 13, 14 are cleaning tanks for cleaning the outside and the inside of the sample probes 11a, 12a after reagent dispensing, each time the sample is to be dispensed. Meanwhile, the cleaning vessels 23, 24 are parts for additional cleaning processing performed on the sample probes 11a, 12a before sample analysis when a measurement request of a pre-registered analysis item is received for a sample of a pre-registered sample type.

The reagent disk 9 is a storage container on which a plurality of reagent bottles 10 each accommodating a reagent therein can be placed on a circumference. The reagent disk 9 is kept cool.

The reagent dispensing mechanisms 7, 8 for dispensing the reagent from the reagent bottle 10 to the reaction vessel are provided, which are configured to be capable of horizontally rotating and moving up and down between the reaction disk 1 and the reagent disk 9, and the reagent dispensing mechanisms 7, 8 respectively include reagent probes 7a, 8a with tips thereof being directed downward. A reagent pump 18 is connected to the reagent probes 7a, 8a. A reagent, a detergent, a diluent, a pretreatment reagent, and the like suctioned from the reagent bottle 10 and the like are dispensed via the reagent probes 7a, 8a into the reaction vessel 2 by the reagent pump 18.

In an operating range of the reagent dispensing mechanism 7, a cleaning tank 32 for cleaning the reagent probe 7a with cleaning liquid is arranged. In an operating range of the reagent dispensing mechanism 8, a cleaning tank 33 for cleaning the reagent probe 8a with cleaning liquid is arranged.

Around the reaction disk 1, the stirring mechanisms 5, 6, the spectrophotometer 4 that measures absorbance of a reaction liquid by measuring transmitted light obtained from the light source 4a via the reaction liquid in the reaction vessel 2, and the cleaning mechanism 3 that cleans the used reaction vessel 2 and the like are arranged.

The stirring mechanisms 5, 6 are configured to be capable of horizontally rotating and moving up and down, and are inserted into the reaction vessel 2 to stir the mixed liquid (reaction liquid) of the sample and the reagent. In operating ranges of the stirring mechanisms 5, 6, cleaning tanks 30, 31 for cleaning the stirring mechanisms 5, 6 with cleaning liquid are arranged. A detergent discharge mechanism 20 is connected to the cleaning mechanism 3.

The control unit 22 is configured by a computer or the like, controls operation of each of the mechanisms described above in the automatic analyzer, and performs calculation processing for obtaining a concentration of a predetermined component in a liquid sample such as blood or urine. In FIG. 1, for the sake of simplicity, apart of the connection between the mechanisms of the automatic analyzer and the control unit 22 is omitted.

The general configuration of the automatic analyzer 100 has been described above. Analysis processing of an examination sample by the automatic analyzer 100 as described above is generally performed in the following order.

First, a sample in the sample vessel 15 placed on the sample rack 16 transported to the vicinity of the reaction disk 1 by the sample transport mechanism 17 is dispensed into the reaction vessel 2 on the reaction disk 1 by the sample probe 11a of the first sample dispensing mechanism 11 or the sample probe 12a of the second sample dispensing mechanism 12. Next, a reagent to be used for analysis is dispensed from the reagent bottle 10 on the reagent disk 9 to the reaction vessel 2, in which the sample is previously dispensed, by the reagent probes 7a, 8a of the reagent dispensing mechanisms 7, 8. Subsequently, a mixed liquid of the sample and the reagent in the reaction vessel 2 is stirred by the stirring mechanisms 5, 6. Then, light generated by the light source 4a is transmitted through the reaction vessel 2 containing the mixed liquid, and light intensity of the transmitted light is measured by the spectrophotometer 4. The light intensity measured by the spectrophotometer 4 is transmitted to the control unit 22 via an A/D converter and an interface. Then, a calculation is performed by the control unit 22 to obtain a concentration of a predetermined component of the analysis item according to the reagent, and a result is displayed on a display unit (not shown) and stored in a storage unit (not shown).

FIG. 2 is a schematic diagram for illustrating an apparatus configuration for performing waste liquid suction operation. First, an apparatus configuration for suctioning waste liquid will be described. When the vacuum pump is operated, pressure in the vacuum tank connected to the vacuum pump is reduced. The vacuum tank is provided with a vacuum switch 36 for sensing that the pressure in the vacuum tank is reduced to specified negative pressure. When the specified negative pressure is reached and the vacuum switch is turned ON, the control unit 22 determines that analysis is possible. The vacuum switch is provided with a pressure receiving portion for receiving pressure and a pressure receiving element for detecting the pressure received by the pressure receiving portion, and is configured with a spring and a switch. When the pressure receiving element senses that the pressure received by the pressure receiving portion reaches a set pressure value, a contact point of the switch is switched by the spring. At an end of the flow path connected to the vacuum tank, reaction waste liquid suction nozzles 37a, 37b or a cleaning waste liquid suction mechanism 39 is provided, and when solenoid valves 35c, 35d between the vacuum tank and the reaction waste liquid suction nozzles 37a, 37b or the cleaning waste liquid suction mechanism 39 are opened, vacuum suction can be performed. Vacuum bottles 34a, 34b for trapping the reaction waste liquid are provided in a flow path of the reaction waste liquid suction nozzles 37a, 37b, and the solenoid valve 35c. When solenoid valves 35a, 35b connected to the vacuum bottles 34a, 34b are opened, the reaction waste liquid is discharged from the vacuum bottles 34a, 34b. The apparatus configuration for suctioning the waste liquid has been described above.

Next, suction operation of the reaction waste liquid will be described. The reaction waste liquid is suctioned by a reaction waste liquid suction mechanism 21. After completion of the analysis, since the reaction waste liquid in which the sample and the reagent are reacted remains in the reaction vessel 2, the reaction disk 1 rotates and the reaction vessel 2 containing the reaction waste liquid is moved to a position of the cleaning mechanism 3. When the cleaning mechanism 3 moves down and the reaction waste liquid suction nozzles 37a, 37b enter the inside of the reaction vessel 2, the solenoid valve 35c connected to the vacuum tank is opened and the reaction waste liquid is suctioned. The suctioned reaction waste liquid is trapped by the vacuum bottles 34a, 34b, and is discharged to a waste liquid tank or a waste liquid sewage facility outside the apparatus by opening the solenoid valves 35a, 35b. In the reaction waste liquid suction nozzle 37a, high concentration reaction waste liquid in which the sample and the reagent are mixed is suctioned. In the reaction waste liquid suction nozzle 37b, low concentration reaction waste liquid is suctioned in which reaction waste liquid is diluted by a detergent discharged by the detergent discharge mechanism 20 during cleaning operation of the reaction vessel 2 after being suctioned. The suction operation of the reaction waste liquid has been described above.

Next, suction operation of the cleaning waste liquid will be described. The cleaning waste liquid is suctioned by a probe cleaning mechanism 40. After dispensing, the second sample dispensing mechanism 12 moves the sample probe 12a to the cleaning tank 14. Cleaning water is discharged from a cleaning water discharge mechanism 14a, and the sample adhered to the surface of the sample probe 12a is washed away. Thereafter, the second sample dispensing mechanism 12 moves the sample probe 12a to the cleaning waste liquid suction mechanism 39. Cleaning water remaining on the surface of the sample probe 12a is suctioned by opening the solenoid valve 35d. Since an amount of cleaning water to be suctioned is extremely small, the cleaning water is trapped in the vacuum tank. The suction operation of the cleaning waste liquid is also performed in the cleaning tank 13 for the first sample dispensing mechanism 11. The suction operation of the cleaning waste liquid has been described above.

In the above configuration, a method for detecting an anomaly such as clogging in a plurality of flow paths connected to the vacuum tank will be described. First, in FIG. 3A, a relationship between negative pressure in the vacuum tank and a signal of the vacuum switch when the vacuum tank is opened to the atmosphere without anomaly such as clogging in the flow path connected to the vacuum tank will be described. A vertical axis represents the negative pressure in the vacuum tank, and a horizontal axis represents time. When the vacuum pump is turned ON, the pressure in the vacuum tank is reduced. When a threshold of the vacuum switch is reached, the vacuum switch 36 is turned ON. The vacuum pump is stopped at any time T in a state in which the negative pressure in the vacuum tank is stable, and one of a plurality of solenoid valves connected to the vacuum tank is opened to bring the vacuum tank into an atmosphere open state. The negative pressure in the vacuum tank in the atmosphere open state decreases, and when the pressure falls below the threshold of the vacuum switch, the vacuum switch is turned OFF. At this time, time $t_n$ that elapses before the vacuum switch is turned OFF from the any time T is measured. After the measurement is completed, the vacuum pump is turned ON and the solenoid valve is closed to make the negative pressure in the vacuum tank constant. The above measurement is performed n times for n solenoid valves connected to the vacuum tank (n=1, 2 . . . , n), and is set in the storage unit as a reference value $t_n$ when there is no clogging in each flow path. Since the reference value $t_n$ is measured and determined at the time of shipment of the apparatus, an individual difference such as an inner diameter of a tube constituting the solenoid valve or the flow path is offset. Therefore, the setting of the reference value $t_n$ is a condition that the measurement is performed with a new flow path configuration.

Next, in FIG. 3B, a relationship between the negative pressure in the vacuum tank and the opening and closing of the solenoid valve connected to the vacuum tank, the ON/OFF of the vacuum pump, and the signal of the vacuum switch 36 when there is an anomaly such as clogging in the flow path connected to the vacuum tank will be described. As in FIG. 3A, the vacuum pump is stopped at any time T, and one of the plurality of solenoid valves connected to the vacuum tank is opened to bring the vacuum tank into the atmosphere open state. When the flow path is clogged, the negative pressure in the vacuum tank in the atmosphere open state decreases more slowly than in the case where there is no clogging, so that time $t_n'$ that elapses before the vacuum switch is turned OFF becomes long. Therefore, since the relationship between the reference values $t_n$ and $t_n'$ is $t_n < t_n'$, clogging can be detected. The method for determining clogging has been described above.

FIG. 4A shows a flowchart of determining clogging in the probe cleaning mechanism 40. As preparation operation, at the start of the flow path clogging determination (S1), all the solenoid valves connected to the vacuum tank are closed (S2). The vacuum pump starts operating (S3), and when the negative pressure in the vacuum tank exceeds a threshold of the vacuum switch, the vacuum switch is turned ON, and the pressure in the vacuum tank becomes constant (S4). At any time T, the vacuum pump is turned OFF (S5). As determination operation, the solenoid valve 35c connected to the vacuum tank is opened (S6). Time $t_1$ that elapses before the vacuum switch is turned OFF is measured (S7), and clogging determination is performed (S8). When it is determined that there is no clogging, the processing moves to analysis operation (S9). When it is determined that there is clogging, a determination result is displayed with an alarm on an operation unit (S10), and the apparatus is stopped (S11). The determination of the clogging is effective even when a plurality of mechanisms that suction cleaning waste liquid are connected to the vacuum tank.

FIG. 4B is a flowchart when the mechanism that suctions the cleaning waste liquid is connected to n or more (n=2) vacuum tanks. As in FIG. 4A, as preparation operation, at the start of the flow path clogging determination (S1), all the solenoid valves connected to the vacuum tank are closed (S2). The vacuum pump starts operating (S3), and when the negative pressure in the vacuum tank exceeds the threshold of the vacuum switch, the vacuum switch is turned ON, and the pressure in the vacuum tank becomes constant (S4). At any time T, the vacuum pump is turned OFF (S5). As determination operation, a solenoid valve in the flow path corresponding to a reference value $t_1$ is opened (S16). Time $t_1$ that elapses before the vacuum switch is turned OFF is measured (S17), and clogging determination is performed (S18). A determination result is stored in a storage unit (S25). After the clogging determination, it is confirmed that the opened solenoid valve is closed (S19), the vacuum pump is turned ON, and the vacuum switch is turned ON (S20). The vacuum pump is stopped and only a solenoid valve corresponding to a reference value $t_2$ is opened (S21). Time $t_2'$ that elapses before the vacuum switch is turned OFF is measured (S22), and clogging determination is performed (S23). By repeating the series of operation n times, clogging determination is performed for each flow path connected to the vacuum tank (S24), and a determination result is displayed (S26). When there is no clogging, the processing moves to the analysis operation (S27). When there is clogging, an alarm is displayed and the apparatus is stopped (S28).

FIG. 5 shows a flowchart of determining clogging when there are n or more (n=2) solenoid valves branched before the solenoid valve 35c connected to the vacuum tank as in the reaction waste liquid suction mechanism 21. As preparation operation, at the start of the flow path clogging determination (S1), all the solenoid valves connected to the vacuum tank are closed (S2). The vacuum pump starts operating (S3), and when the negative pressure in the vacuum tank exceeds the threshold of the vacuum switch, the vacuum switch is turned ON, and the pressure in the vacuum tank becomes constant (S4). At anytime T, the vacuum pump is turned OFF (S5). As determination operation, only the solenoid valve 35c connected to the vacuum tank is opened (S36). Time that elapses before the vacuum switch is turned OFF is measured (S37), and the clogging determination is performed (S38). When there is no clogging, the processing moves to the analysis operation (S30). When there is clogging, the opened solenoid valve is closed (S39), and it is confirmed that the vacuum pump is turned ON, and the vacuum switch is turned ON (S40). The vacuum pump is turned OFF, and the solenoid valve 35c and one of the branched solenoid valves (solenoid valve 35a) are simultaneously opened (S41). Time that elapses before the vacuum switch is turned OFF is measured (S42), and the clogging determination is performed (S43). By repeating the series of operation n times, the clogging determination is performed for each of the branched flow paths (S44), and the determination result is displayed with an alarm (S46), and the apparatus is stopped (S47).

The clogging determination operation and the flowchart are performed at the time of analysis preparation and maintenance. In particular, the time that elapses before the vacuum switch is turned OFF measured at the time of maintenance is recorded in the apparatus such that the measured time can be compared with a previous value every time the maintenance is performed. By recording the measured time that elapses before the vacuum switch is turned off from the time of shipment, deterioration of each flow path can be grasped, and the clogging determination operation can be used as a preventive maintenance function.

FIG. 6 shows a relationship between the pressure in the vacuum tank and an altitude when the clogging determination method is used. Since atmospheric pressure is lower in an area at an altitude of 2000 m than that at an altitude of 0 m, the vacuum pump cannot sufficiently draw negative pressure, and there is no margin for the suction operation of the waste liquid using the vacuum. Therefore, when the vacuum pump is stopped in a state in which the negative pressure in the vacuum tank is constant, all the solenoid valves connected to the vacuum tank are opened, and the vacuum tank is opened to the atmosphere, assuming that a reference value until the vacuum switch at an altitude h is turned off is $t_h$, $t_0 > t_{2000}$. A reference value $t_h$ corresponding to the altitude is set in the apparatus as a value unified for all apparatuses, and time $t_h'$ that elapses before the vacuum switch is turned OFF when the apparatus is installed is measured and is compared with the reference value $t_h$. When the comparison result is $t_h > t_h'$, since it can be determined that there is no margin for the suction operation of waste liquid using vacuum, it is possible to determine a correspondence such as adding a vacuum pump or replacing the vacuum pump with a vacuum pump capable of drawing a high vacuum degree.

Further, by using the reference value $t_h$, it is possible to individually set atmosphere open time at the time of analysis completion operation in accordance with the altitude of the installation destination of the apparatus. In the automatic analyzer, it is common to return the pressure inside of the vacuum tank to the atmospheric pressure during the analysis completion operation. This is because if negative pressure remains in the vacuum tank, the vacuum pump is always applied with negative pressure, a load is applied to actuate the diaphragm from a negative pressure state when the vacuum pump is started, and deterioration of the vacuum pump is accelerated. When an altitude h of an installation location is input to the apparatus, the reference value $t_h$ as the time required to return the pressure in the vacuum tank to the atmospheric pressure according to the altitude can be set as the atmosphere open time of the analysis completion operation. Accordingly, waiting time of an operator can be shortened by completing the analysis completion operation at appropriate time.

REFERENCE SIGN LIST 1 reaction disk
2 reaction vessel
3 cleaning mechanism
4 spectrophotometer
4a light source
5, 6 stirring mechanism
7, 8 reagent dispensing mechanism
7a, 8a reagent probe
9 reagent disk
10 reagent bottle
11 first sample dispensing mechanism
11a sample probe
12 second sample dispensing mechanism
12a sample probe
13, 14 cleaning tank
14a cleaning water discharge port
15, 15a, 15b sample vessel
16 sample rack
17 sample transport mechanism
18a reagent pump
19 sample pump
20 detergent discharge mechanism
21 reaction waste liquid suction mechanism
22 control unit
23, 24 cleaning vessel
30, 31, 32, 33 cleaning tank
34a, 34b vacuum bottle
35a, 35b, 35c, 35d solenoid valve
36 vacuum switch
37a, 37b reaction waste liquid suction nozzle
39 cleaning waste liquid suction mechanism
40 probe cleaning mechanism
100 automatic analyzer

The invention claimed is:

1. An automatic analyzer comprising:
a vacuum tank and a vacuum pump that vacuum suctions liquid;
a first solenoid valve provided in a flow path connected to the vacuum tank;
a vacuum switch provided in the vacuum tank, the vacuum switch comprising a pressure receiving portion having a spring which senses a pressure value present in the vacuum tank and which switches a contact point of the vacuum switch when the sensed pressure reaches a set value; and
a processor coupled to the vacuum pump, the first solenoid valve, and the vacuum switch,
wherein the processor is configured to
receive a signal from said vacuum switch indicating the pressure value present within said vacuum tank;
determine whether said received pressure value in the vacuum tank is equal to or greater than a predetermined pressure value threshold, or whether said received pressure value is smaller than the predetermined pressure value threshold; and
detect clogging in the flow path
by executing a sequence of programmed instructions which
change the vacuum pump from ON to OFF with the first solenoid valve being in a closed state, and
thereafter, change the first solenoid valve from the closed state to an open state, and detect presence and absence of clogging in the flow path by comparing, to a first predetermined time threshold, a time that elapses before the processor determines that said received pressure value in the vacuum tank is equal to or greater than the predetermined pressure value threshold from a time point when the first solenoid valve is changed from the closed state to the open state based on the signal received from the vacuum switch indicating that the spring of the pressure sensing portion of the vacuum switch has switched the contact point of the vacuum switch;

a plurality of waste liquid bottles each accommodating waste liquid from a side closer to the vacuum tank, and a reaction vessel, on an opposite side of the first solenoid valve with respect to the vacuum tank, wherein each said waste liquid bottle is provided with a second solenoid valve on a discharge side from which waste liquid is discharged, and a second flow path from the reaction vessel to the vacuum tank is provided for each of the waste liquid bottles, wherein when the processor determines that the flow path is clogged, the processor is further configured to close the first solenoid valve, change the vacuum pump from OFF to ON, confirm that the received pressure value in the vacuum tank is smaller than the predetermined pressure value threshold, and thereafter, change the vacuum pump from ON to OFF, change the first solenoid valve and any one of the second solenoid valves from the closed state to the open state, and detect presence and absence of the clogging in the flow path by comparing, to a second predetermined time threshold, a time that elapses before the processor determines that the received pressure value in the vacuum tank is equal to or greater than the predetermined pressure value threshold from a time point when the valves are changed from the closed state to the open state based on the signal received from the vacuum switch indicating that the spring of the pressure sensing portion of the vacuum switch has switched the contact point of the vacuum switch.

2. The automatic analyzer according to claim 1, further comprising:

a cleaning waste liquid suction mechanism that suctions cleaning liquid on a surface of a sample probe by the vacuum pump, on an opposite side of the first solenoid valve with respect to the vacuum tank.

3. The automatic analyzer according to claim 2, further comprising:

a cleaning tank that accommodates cleaning liquid for a reagent probe and that is adjacent to the cleaning waste liquid suction mechanism.

4. The automatic analyzer according to claim 1, wherein a plurality of combinations of the first solenoid valve and the flow path are provided, and the processor is configured to sequentially perform the clogging detection for each flow path by controlling opening and closing of the first solenoid valve.

5. The automatic analyzer according to claim 1, wherein which flow path is clogged is detected by sequentially performing operation of changing the first solenoid valve and any one of the second solenoid valves from the closed state to the open state.

6. The automatic analyzer according to claim 1, wherein the pressure value threshold used when the clogging is detected is set based on a height of an altitude at which the apparatus is installed.

7. A method for detecting flow path clogging of an automatic analyzer comprising:

controlling, using a processor, a vacuum pump that vacuum suctions liquid from a vacuum tank;

controlling, by the processor, a first solenoid valve provided in a flow path connected to the vacuum tank;

receiving a signal from a vacuum switch provided in the vacuum tank, the vacuum switch comprising a pressure receiving portion having a spring which senses a pressure value present in the vacuum tank and which switches a contact point of the vacuum switch when the sensed pressure reaches a set value;

determining, by the processor, whether the pressure value in the vacuum tank is equal to or greater than a predetermined pressure threshold, or whether the pressure value is smaller than the predetermined pressure threshold; and detecting clogging in the flow path, by the processor by changing the vacuum pump from ON to OFF with the first solenoid valve being in a closed state, and thereafter, changing the first solenoid valve from the closed state to an open state, and detecting presence and absence of clogging in the flow path by comparing, to a first predetermined time threshold, a time that elapses before the processor determines that the pressure value in the vacuum tank is equal to or greater than the predetermined pressure threshold from a time point when the first solenoid valve is changed from the closed state to the open state based on the signal received from the vacuum switch indicating that the spring of the pressure sensing portion of the vacuum switch has switched the contact point of the vacuum switch a plurality of waste liquid bottles each accommodating waste liquid from a side closer to the vacuum tank, and a reaction vessel, on an opposite side of the first solenoid valve with respect to the vacuum tank, wherein each said waste liquid bottle is provided with a second solenoid valve on a discharge side from which waste liquid is discharged, and a second flow path from the reaction vessel to the vacuum tank is provided for each of the waste liquid bottles, wherein when the processor determines that the flow path is clogged, closing the first solenoid valve, changing the vacuum pump from OFF to ON, confirming that the received pressure value in the vacuum tank is smaller than the predetermined pressure value threshold, and thereafter, changing the vacuum pump from ON to OFF, changing the first solenoid valve and any one of the second solenoid valves from the closed state to the open state, and detecting presence and absence of the clogging in the flow path by comparing, to a second predetermined time threshold, a time that elapses before the processor determines that the received pressure value in the vacuum tank is equal to or greater than the predetermined pressure value threshold from a time point when the valves are changed from the closed state to the open state based on the signal received from the vacuum switch indicating that the spring of the pressure sensing portion of the vacuum switch has switched the contact point of the vacuum switch.

* * * * *